(12) United States Patent
Fairchild

(10) Patent No.: US 7,800,752 B2
(45) Date of Patent: Sep. 21, 2010

(54) WAVELENGTH DEPENDENT REFLECTIVE SAMPLE SUBSTRATES FOR RAMAN AND FLUORESCENCE SPECTROSCOPY

(75) Inventor: Ronald C. Fairchild, Ann Arbor, MI (US)

(73) Assignee: Kaiser Optical Systems, Ann Arbor, MI (US)

( * ) Notice: Subject to any disclaimer, the term of this patent is extended or adjusted under 35 U.S.C. 154(b) by 565 days.

(21) Appl. No.: 11/747,477

(22) Filed: May 11, 2007

(65) Prior Publication Data

US 2008/0278719 A1    Nov. 13, 2008

(51) Int. Cl.
*G01J 3/44*    (2006.01)
(52) U.S. Cl. .................................................... 356/301
(58) Field of Classification Search ................. 356/301, 356/246
See application file for complete search history.

(56) References Cited

U.S. PATENT DOCUMENTS 7,349,093 B2 *    3/2008    Tabata et al. ................. 356/417

* cited by examiner

*Primary Examiner*—Tarifur Chowdhury
*Assistant Examiner*—Abdullahi Nur
(74) *Attorney, Agent, or Firm*—Gifford, Krass, Sprinkle, Anderson & Citkowski, P.C.

(57) ABSTRACT

A material which is generally transparent in the visible region of the spectrum but reflective at laser wavelengths reduces undesirable, substrate-induced Raman and fluorescence scattering. A substrate provides a surface for supporting the sample, with the material being disposed between the surface of the substrate and the sample. The material is substantially transparent in the visible region of the spectrum but reflective at the laser wavelength, thereby minimizing unwanted Raman or fluorescence scattering that would be produced by the substrate if the material were not present. The substrate will typically be a glass microscope slide or multi-cell well plate. The optical filter material is preferably a multilayer dielectric filter acting as a "hot mirror" that reflects near-infrared energy. An advantage of visible transmission is that it allows back illumination from behind/underneath the slide or well plate, thereby being visible to a microscope's eyepiece or video camera. Methods and article are also disclosed.

13 Claims, 2 Drawing Sheets

WAVELENGTH DEPENDENT REFLECTIVE SAMPLE SUBSTRATES FOR RAMAN AND FLUORESCENCE SPECTROSCOPY

FIELD OF THE INVENTION

This invention relates generally to Raman and fluorescence microscopy and, in particular, to apparatus and method for reducing undesirable substrate-induced scattering in systems of this type.

BACKGROUND OF THE INVENTION

It is common to use a glass slide to hold a material of interest (sample) when performing Raman or fluorescence microscopy. Referring to FIG. 1, a problem arises in that an interfering spectrum 120 from the glass 102 can overwhelm the desired spectrum 112 from the sample 100, especially if (a) not much sample is present; (b) the probe has a larger spot size than the sample; and/or (c) the sample is transparent and is a weak Raman/fluorescence scatterer. In an attempt to solve this problem, researchers will sometimes wrap the slide in aluminum foil to shield the glass from the laser 110.

SUMMARY OF THE INVENTION

This invention solves the above-referenced problem through the use of a material which is generally transparent in the visible region of the spectrum but reflective at the laser wavelength. In a typical configuration, a substrate provides a surface for supporting the sample, with the material being disposed between the surface of the substrate and the sample. The material is substantially transparent in the visible region of the spectrum but reflective at the laser wavelength, thereby minimizing unwanted Raman or fluorescence scattering that would be produced by the substrate if the material were not present.

In preferred embodiments the substrate is a microscope slide, dimpled sample holder or multi-cell well plate. Although other materials such as polymer may be used, such substrates are ordinarily glass. Although other types of optical filters such as holographic filters may be used, in the preferred embodiment the material is a multilayer dielectric filter acting as a "hot mirror" that reflects near-infrared energy. For laser wavelengths in manufacturing environments, a useful material becomes reflective above 700 nm or thereabouts.

Both surfaces of the substrate may include the optical filter material so that either side of the substrate may be used to support the sample. Although a full-spectrum mirror coating would work to protect the substrate from laser energy, an advantage of visible transmission is that it allows back illumination from behind/underneath the slide or well plate, thereby being visible to a microscope's eyepiece or video camera. In addition, polarization microscopy may still be employed to locate regions of interest in the sample.

A method of investigating a sample according to the invention comprises the steps of placing the sample on the surface of a substrate having an optical filter with a transmissive wavelength region and a reflective wavelength region; illuminating the sample with a laser having a wavelength in the reflective wavelength region; and analyzing the Raman or fluorescence scattering from the sample resulting from the laser illumination.

DETAILED DESCRIPTION OF THE INVENTION

As discussed in the Summary, this invention uses a layer of laser-reflective material on a glass substrate such that when material of interest is present on the coating, the glass is essentially hidden from the laser illumination and thus little if any unwanted Raman or fluorescence scattering is produced.

In the preferred embodiment, a "hot minor" dielectric coating is applied to one or both glass surfaces. A useable hot mirror coating includes that sold by Edward Scientific, e.g. item #M43-843 on page 79 of its 2007 catalog #N071A. Such a coating is generally transparent in the visible and at least slightly reflective in the mean IR region above 700 nm or thereabouts.

Figure 1:
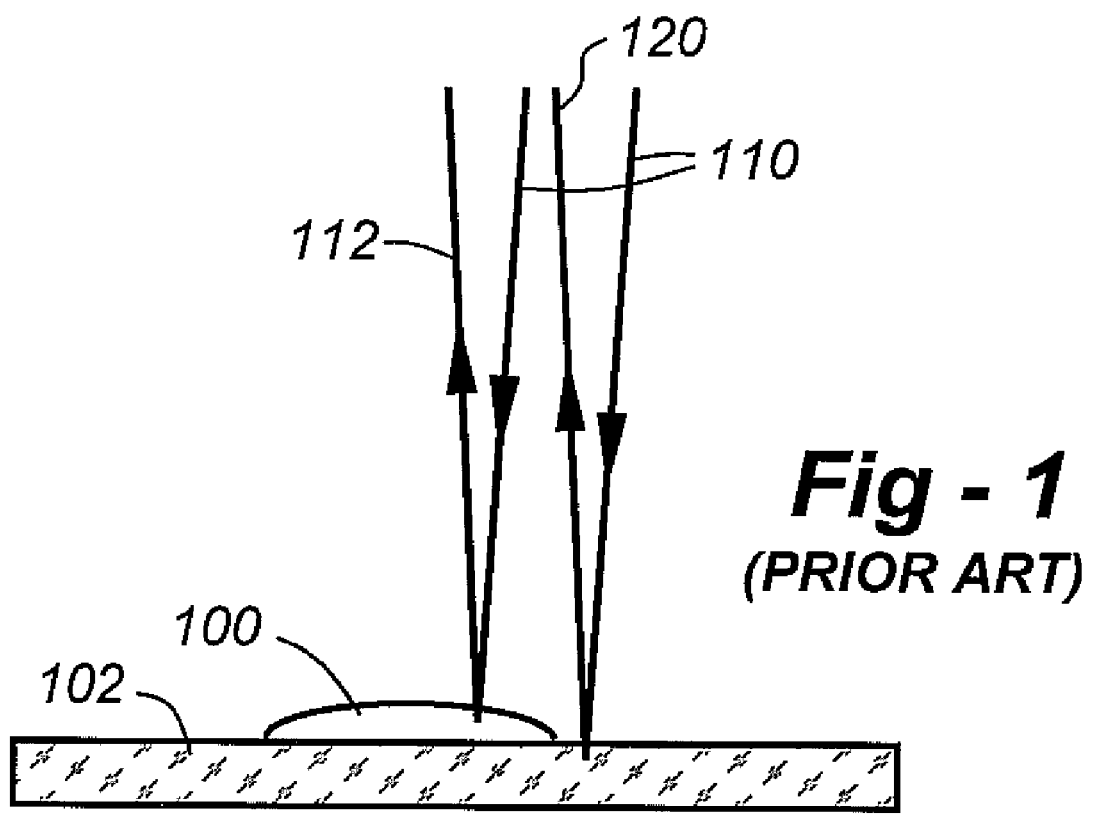
FIG. 1 is a drawing that illustrates a current problem associated with obtaining Raman or fluorescence spectra from a sample placed on a glass slide.
Figure 2:
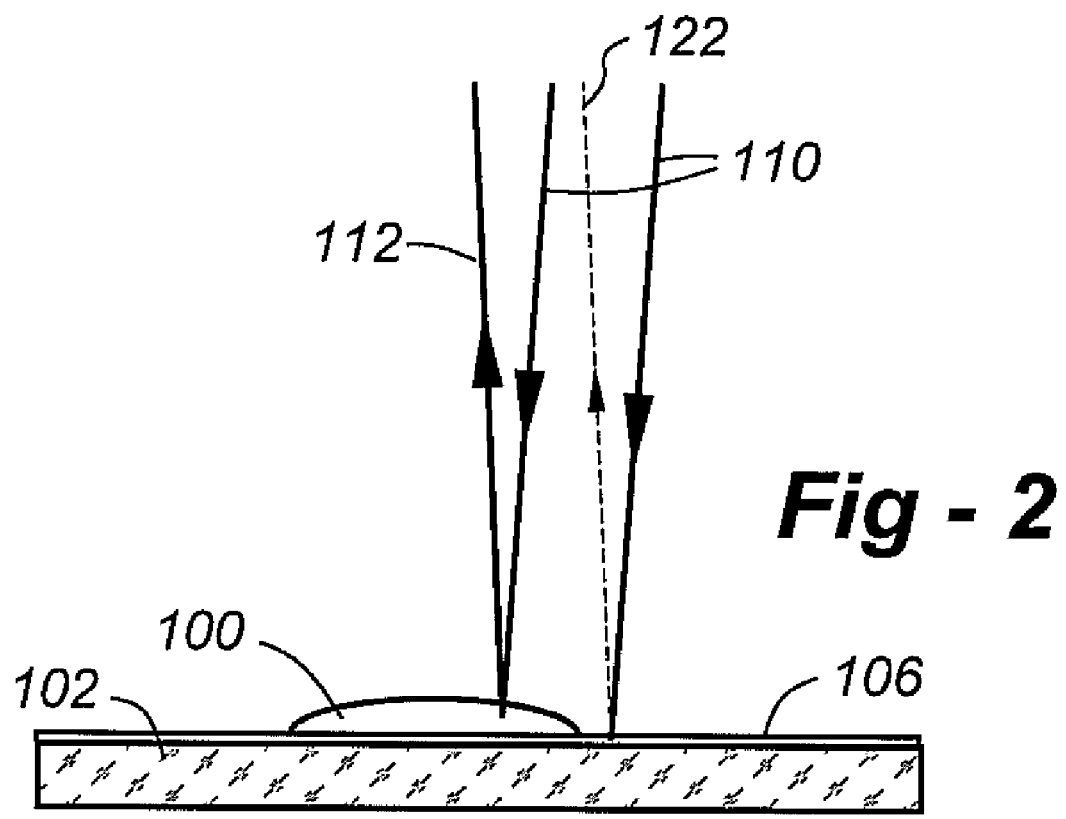
FIG. 2 is a drawing that shows how the problem associated with FIG. 1 is solved in accordance with the invention.

Referring to FIG. 2, when a substitute substrate according to the invention is used by placing the sample directly on the appropriate layer or coating 106, the glass 102 is essentially hidden from the laser illumination 110 and thus no Raman or fluorescence scattering 122 is produced.

An added advantage of the coating is that the desired scattering that can be collected from the material of interest will be increased by as much as a factor of four due to 1) backscatter from direct illumination; 2) forward scatter from the direct illumination that is reflected back by coating; 3) forward scatter from laser illumination that is reflected back by the coating; and 4) backscatter from the laser illumination (as in 3, above) which is then reflected back by the dielectric.

Another advantage is that any Raman or fluorescence scattering produced by laser illumination that leaks through the filter to the substrate material is also reflected back by the filter and thus does not interfere with scattering from the sample.

Another advantage is that the material of interest can be observed in the visible spectrum through the back of the substrate, e.g. with an inverted microscope, or can be illuminated in the visible from the back for transmission imaging.

Another advantage is that polarization microscopy may still be employed to locate regions of interest in the sample since polarized illumination in the visible spectrum coming from beneath the substrate will pass through the filter largely unaffected.

Figure 3:
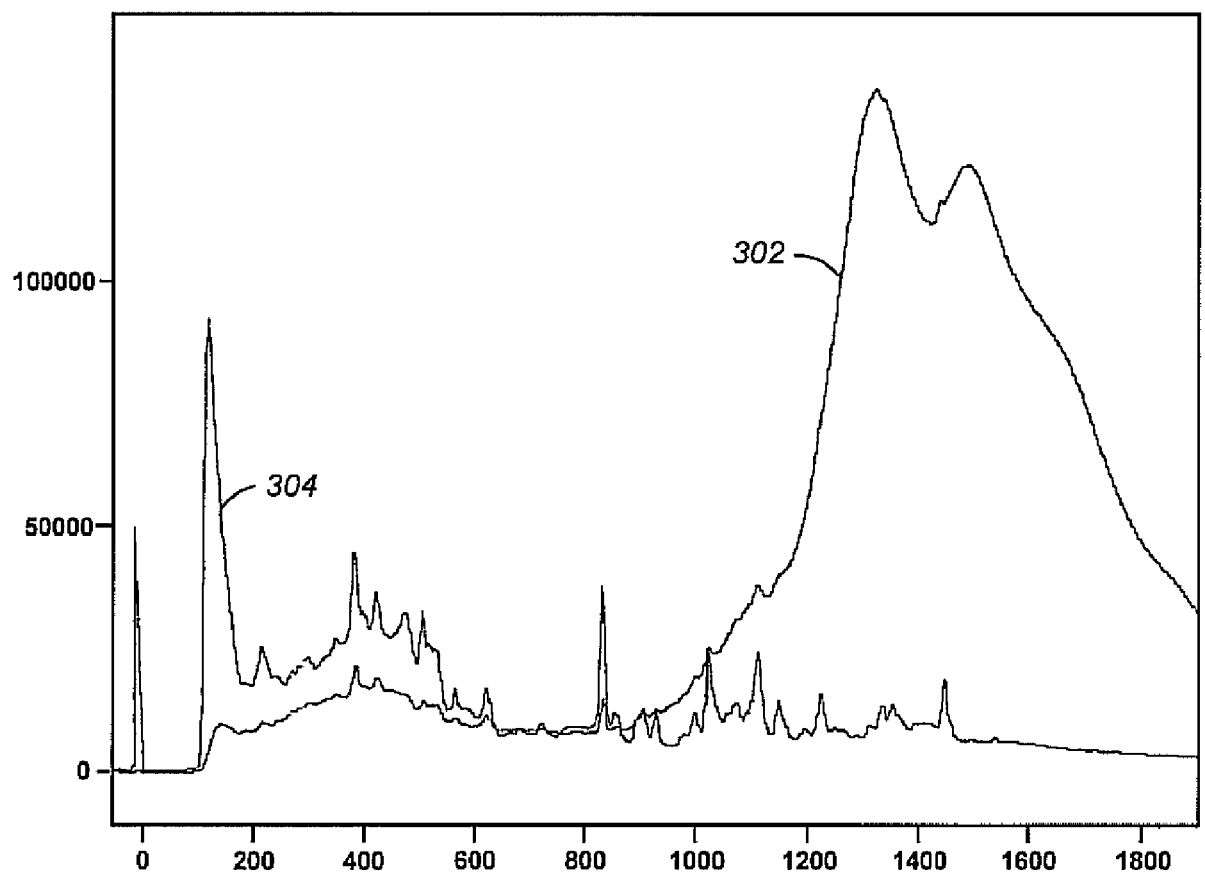
FIG. 3 compares Raman spectra obtained for crystal sugar on a glass substrate with and without a coating according to the invention.

FIG. 3 shows two spectra collected of a sugar crystal using a PhAT Raman Analyzer available from Kaiser Optical Systems. Inc. (785 nm excitation, 1-mm spot size). In curve 302, the crystal was placed on the uncoated side of a "hot minor" coated substrate. The exposure was for 1 second. In the other curve, 304, the crystal was placed on the coated side of the same hot mirror and used a 10 second exposure. Clearly, the sugar Raman peaks are much better resolved, especially at longer wave shifts.

An extension of the invention is with well plates. Glass (quartz) well plates are often used with inverted microscopes at high magnification looking through the bottom of the well plate, since the high magnification objectives generally have short working distances. Long working distance objectives can be used with Raman through the open end of the well, however, silica Raman from the well plate bottom can overwhelm the Raman from the material of interest which is often just a few small crystals at the bottom of the well. The solution is to add a dielectric "hot minor" coating to the bottom of the wells.

I claim:

1. A spectrographic system for use with a sample under investigation, comprising:
   a substrate having an upper surface for supporting the sample;
   a laser having a wavelength directed to the sample from above the substrate;
   a detector to receive Raman scattering from the sample above the substrate; and
   an optical filter disposed between the upper surface of the substrate and the sample, the filter being substantially reflective at the laser wavelength, thereby minimizing unwanted Raman scattering at the detector that would be produced by the substrate if the filter were not present.

2. The system of claim 1, wherein the substrate is a microscope slide.

3. The system of claim 1, wherein the substrate is a glass microscope slide.

4. The system of claim 1, wherein the substrate is a dimpled plate.

5. The system of claim 1, wherein the substrate is a dimpled glass plate.

6. The system of claim 1, wherein the substrate is a multi-cell well plate.

7. The system of claim 1, wherein the substrate is a glass multi-cell well plate.

8. The system of claim 1, wherein the substrate is a polymer multi-cell well plate.

9. The system of claim 1, wherein the filter is a multilayer dielectric filter.

10. The system of claim 1, wherein the filter is a "hot mirror" that reflects near-infrared energy.

11. The system of claim 1, wherein the filter becomes reflective above 700 nm or thereabouts.

12. The system of claim 1, wherein:
   the substrate has a lower surface; and
   further including a microscope for imaging the sample in the visible region of the spectrum through the lower surface of the substrate.

13. The system of claim 12, wherein the illumination through the lower surface is polarized visible light to facilitate polarization microscopy as a means for identifying regions of interest in the sample.

* * * * *